(12) United States Patent
August et al.

(10) Patent No.: US 6,530,288 B1
(45) Date of Patent: Mar. 11, 2003

(54) MICROCOLUMN FOR USE IN SAMPLE EXTRACTION

(75) Inventors: Thomas F. August, Glenolden, PA (US); Michael J. Telepchak, Yardley, PA (US)

(73) Assignee: United Chemical Technologies, Inc., Bristol, PA (US)

( * ) Notice: Subject to any disclaimer, the term of this patent is extended or adjusted under 35 U.S.C. 154(b) by 229 days.

(21) Appl. No.: 09/599,680

(22) Filed: Jun. 22, 2000

(51) Int. Cl.⁷ .................................................. G01N 1/00
(52) U.S. Cl. .................................................. 73/863.31
(58) Field of Search ...................... 73/38, 61.52, 61.53, 73/61.55, 61.58, 863.21, 863.23; 210/656, 266, 282, 455; 96/105–107; 422/70, 89

(56) References Cited

U.S. PATENT DOCUMENTS

| | | | | |
|---|---|---|---|---|
| 4,116,845 A | * | 9/1978 | Swank | |
| 4,309,286 A | * | 1/1982 | Lenihan, Jr. et al. | ...... 73/61.53 |
| 5,368,729 A | | 11/1994 | Stefkovich et al. | |
| 5,439,593 A | | 8/1995 | Price | |
| 5,454,951 A | | 10/1995 | Hoopman | |
| 5,503,740 A | * | 4/1996 | Callaghan et al. | |
| 5,658,800 A | | 8/1997 | Lessard et al. | |
| 5,792,354 A | | 8/1998 | Aksberg | |
| 5,849,249 A | | 12/1998 | Jones, Jr. et al. | |

* cited by examiner

*Primary Examiner*—Robert Raevis
(74) *Attorney, Agent, or Firm*—Robert A. Koons, Jr. Esq.; Matthew P. McWilliams; Buchanan Ingersoll, P.C.

(57) ABSTRACT

A housing is described for use in preparing a sample for chemical analysis, the housing having a sample entrance, a sample exit, and a passageway therebetween; the housing further comprising at least three ridges, the ridges integral with the housing, depending into the passageway, and defining a supporting profile for holding a sorbent retaining member.

15 Claims, 2 Drawing Sheets

MICROCOLUMN FOR USE IN SAMPLE EXTRACTION

FIELD OF THE INVENTION

The present invention relates to construction of columns and cartridges for use in preparing samples for chemical analysis, such as for chromatographic analysis. In particular, the construction of the present invention relates to housings such as microcolumns and cartridges, that are useful for separating an analyte of interest from a sample solution. The invention is adaptable for providing a wide variety of microcolumn and cartridge embodiments that can be easily adapted for separation of a range of selected analytes from solution.

BACKGROUND OF THE INVENTION

A wide range of devices for use in containing a sorbent material for use in solid phase extraction of samples in chemical analysis are known. Some of these devices are in the form of cartridges and some are in the form of miniature chromatography columns. These devices provide a housing for a sorbent material, with the sorbent material being retained within the housing during flow of a fluid such as a solvent through the sorbent material by a porous retaining element. The porous retaining element is usually described as being a frit. The frit may be a porous glass plate, a porous polymeric plate, or a supported porous membrane. These various types of frits may be held within the housing of the extraction device by a constriction or narrowing of the housing. The present invention discloses a new construction for extraction devices, that comprises a new way of supporting a porous retaining element for a sample extraction device.

An example of a typical sorbent retaining construction that has been used in the prior art may be seen in U.S. Pat. No. 5,368,729 to Stefkovich et al. This patent discloses a sample extraction device in the form of a column, and having a constriction at its lower end. The constriction forms a shoulder, upon which a frit is supported, the frit serving to retain a solid phase sorbent used for extraction of a sample.

Another example of a device that is known in the art for extraction of a sample is disclosed in U.S. Pat. No. 5,658,800 to Lessard et al. This patent discloses a cartridge in the form of a column, the cartridge containing layers of a sorbent material. The layers are retained within the cartridge during use for sample extraction by "frits or filters." Retention of the sorbent layers appears to be by having a constriction in the bottom of the cartridge, or by having the frit or "filter dimensioned to fit snugly within the inner diameter of the barrel" of the cartridge. This indicates that the element for retaining a sorbent in the cartridge, as disclosed by Lessard, is held in place in the cartridge by a close fit of the element to the inner diameter of the barrel of the cartridge, or of the inner diameter of the barrel to the element.

A construction for retaining a sorbent material within an extraction device was disclosed in U.S. Pat. No. 5,454,951 to Hoopman, that provides a disk shaped element having concentric, radially-spaced apart grooves. The disk shaped element disclosed there uses the grooves and the a plurality of radially-extending grooves to control the flow of liquid from a sorbent layer through a tortuous path above the disk shaped element, to peripherally-located openings in the disk shaped element. In Hoopman there is no teaching of a support for this disk shaped element.

The retaining members known in the art for retaining a sorbent within a cartridge or column, have generally been simple constrictions near the bottom of the cartridge or column. The simple constrictions provide support for a rigid frit, that serves to retain a sorbent material within the cartridge or column, with the frit being porous to allow flow of a solvent through the sorbent and the device. It is known to users of such devices that when a solvent is passed through the device, sputtering of the solvent sometimes occurs below the frit, leading to the elution of a sample being less clean than the user wishes. That is, cross-contamination of samples being eluted from such devices is known to be a problem. Also, it is known in the art that the passage of a solvent through such devices is sometimes subject to channeling effects through the sorbent that make the desired separations below the optimum that might be achieved. There remains a need in the art for a housing for use in sorbent based analytical sample preparation that can be manufactured economically, is adaptable to varied embodiments, and that provides support for a sorbent retaining frit while reducing the sputtering that occurs with known devices. The housing of the present invention as described herein meets these needs.

To overcome the shortcomings of known extraction cartridges and columns, we have now designed a new housing for containing a solid phase extraction sorbent.

SUMMARY OF THE INVENTION

Briefly, a housing construction is disclosed here that can be used to retain a sorbent material within an extraction device. The new construction is for a housing that comprises a plurality of projections within the housing, these projections providing a supporting profile to support a retention member, the retention member supporting the sorbent material used in the housing for purposes of preparing a sample for a chemical analysis.

The new housing can be used for containing a sorbent used in chemical analysis sample preparation. This housing may be used in the form of a column, a cartridge, or an extraction module.

The extraction device of the present invention can be made from any material that is not appreciably soluble in the solvents used for chemical analysis. Examples of some materials that are acceptable with commonly used solvents include glass, polypropylene, polyethylene, polytetrafluoroethylene, and stainless steel. Preferred materials for use with the invention include polyolefin resins, such as polypropylene and polyethylene. More preferably, the inventive extraction device is constructed of a polymeric resin, such as a polypropylene. An example of a polymeric resin that is especially preferred for use with the present invention is a polymeric resin such as Aristech™ F120F, available from Aristech Chemical Corp., 210 Sixth Ave., Pittsburgh, Pa. 15222, U.S.A. The use of a resin such as the indicated resin allows the housing to have a reduced degree/ level of plasticizers or other polymer additives in contact with a fluid/solvent used in chemical analysis.

It is accordingly an aspect of the invention to provide a housing for a sorbent used in analytical sample preparation where the housing incorporates the ability to support the sorbent with a sorbent retention member using spaced apart ridges projecting from the housing.

It is another aspect of the invention to provide a sample extraction device that can be manufactured easily from a polymer resin.

It is another aspect of the invention to provide a sample extraction device that is made with a construction that provides for support of a sorbent retention member, and that provides for channeled flow of a solvent fluid from the sorbent retention member out of the extraction device.

These aspects, and others set forth more fully below are achieved by the present invention.

DETAILED DESCRIPTION OF THE INVENTION

Figure 1:
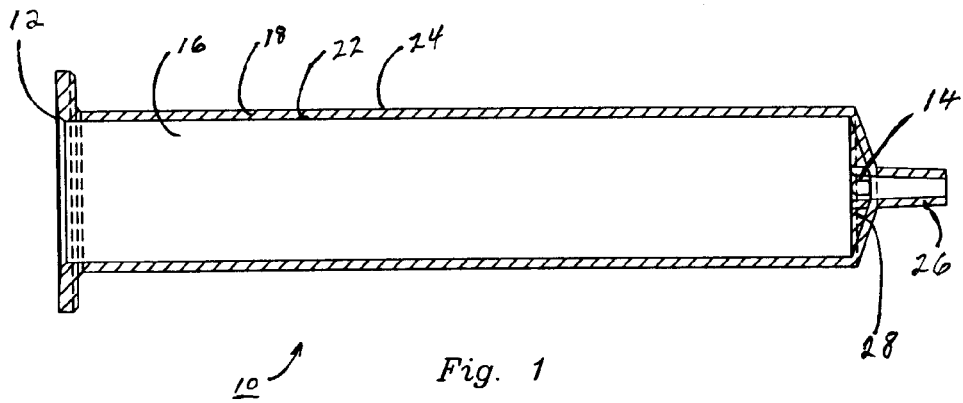
FIG. 1 is an illustration of a sectional side view of an embodiment of a housing according to the invention.

The new housing disclosed here will be readily understood by those skilled in the art, by considering the following example. The example illustrates a preferred embodiment of the new housing. This embodiment is depicted in the accompanying drawings. With reference to these drawings, wherein like reference numerals designate similar parts throughout the various views, this embodiment will now be considered.

FIG. 1 depicts a housing 10 in accordance with the present invention. The housing for this particular embodiment is generally tubular, and in the form of a column such as those used for chromatographic separations. It is to be understood that the housing of the present invention need not be generally tubular to be operative. Other shapes for the housing will be contemplated by those skilled in the art, and the aspect ratio for the housing of the shape shown may be varied while keeping with the teaching and spirit of the invention. These other shapes and aspect ratios are to be included in the scope of the appended claims.

The housing 10 of FIG. 1 comprises a sample entrance 12, and a sample exit 14. Between the sample entrance 12 and the sample exit 14 is a passageway 16 for flow of a fluid from that entrance to that exit. For the embodiment shown, the housing also comprises a wall 18 having an inner surface 22 and an outer surface 24. The wall inner surface 22 defines the passageway 16 and provides space for containing a sorbent to be used with the housing. In normal use of the housing 10 with flow of fluid provided at least in part by gravity, the end to the left of FIG. 1 would be the upper end, and the end to the right of FIG. 1 would be the bottom end.

Disposed at the sample exit 14 of this embodiment is a male Luer™ fitting 26 that is in fluid communication with the passageway 16, and with the male Luer™ fitting depending from the sample exit 14. A preferred embodiment of the new housing will comprise at least one Luer™ fitting. Having a male Luer™ fitting extending from the sample exit allows a user to conveniently connect the housing to various types of laboratory apparatus when using the housing for carrying out a sample preparation. Thus, this fitting is optional but preferred. Optionally, the new housing may be constructed using either or both male and female Luer™ fittings. Also optionally, Luer-Lok™ fittings may be used.

Figure 2:
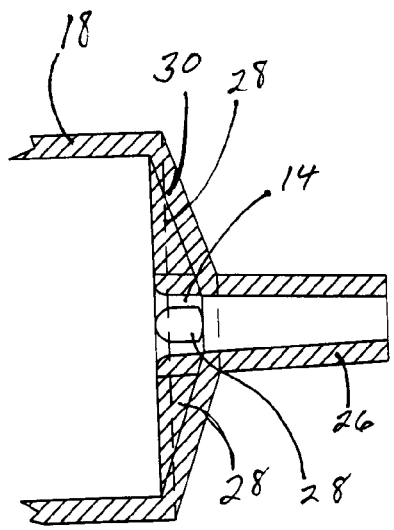
FIG. 2 is an illustration of a sectional side view of a detail of the embodiment of FIG. 1.

Also shown in FIG. 1 is a plurality of projections from the wall inner surface 22 that serve to support a sorbent retaining member (not shown in FIG. 1). FIG. 2 shows an enlarged view of the detail of the housing embodiment, in the vicinity of the sample exit 14. One of the plurality of projections 28 is indicated in FIG. 2. It is to be understood that a housing according to the present invention will comprise a plurality of these projections 28. Preferably, a housing according to the present invention comprises at least three of these projections 28, and more preferably comprises four of these projections 28.

The projections 28 are spaced apart. In the embodiment shown they are ridge-shaped, or elongated, and they are disposed radially in the passageway 16.

The new housing is of unitary construction. The projections 28 that support the sorbent retention element are integral with the housing. These projections 28 are continuous with the housing 10 and depend from the wall inner surface 22 into the interior of the housing. This allows the housing to be made as a one piece unit, preferably by an injection molding process, as would be known to one skilled in the art of injection molding, and the housing provides the cost savings associated with articles that are molded in one piece.

In FIG. 2 may be seen more clearly a sectional side view detail of the embodiment of FIG. 1. The male Luer™ fitting 26 extends from the sample exit 14.

In this particular embodiment there are four projections 28 from the housing, with three of these visible in the sectional side view of FIG. 2. The projections depend upwardly from an inward turning 30 of the wall 18.

Figure 3:
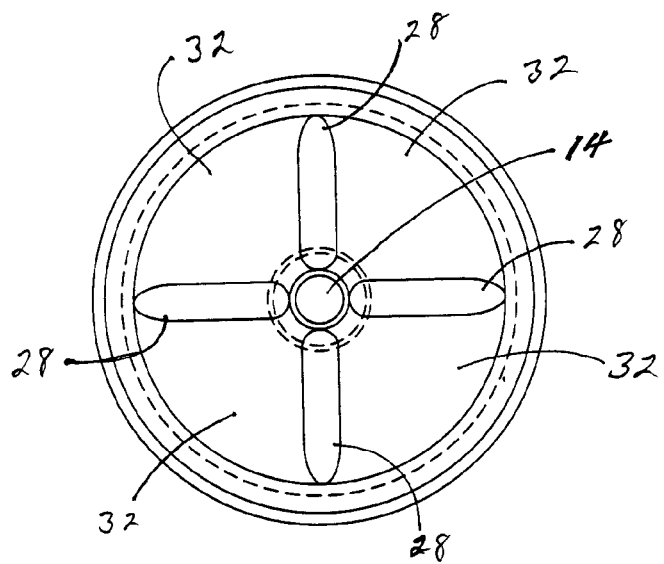
FIG. 3 is an illustration of a sectional top view of the embodiment of FIG. 1.

Turning to FIG. 3, it is seen that the four projections 28 of this embodiment are disposed radially in the passageway. The spaced apart projections 28 form channels 32 in the spaces between the projections. These channels 32 are in fluid communication with the passageway 16 and with the sample exit 14. The projections 28 form an imaginary supporting profile for a porous frit or sorbent retaining member (not shown here). It is preferred that the supporting profile be substantially planar for supporting a sorbent retaining member that is planar. When a sorbent retaining member is above and against the projections 28, and the sorbent retaining member is closely received within the defining inner wall 22 of the passageway 16, any fluid passing through the sorbent retaining member may flow through the channels 32 to the sample exit 14.

Figure 4:
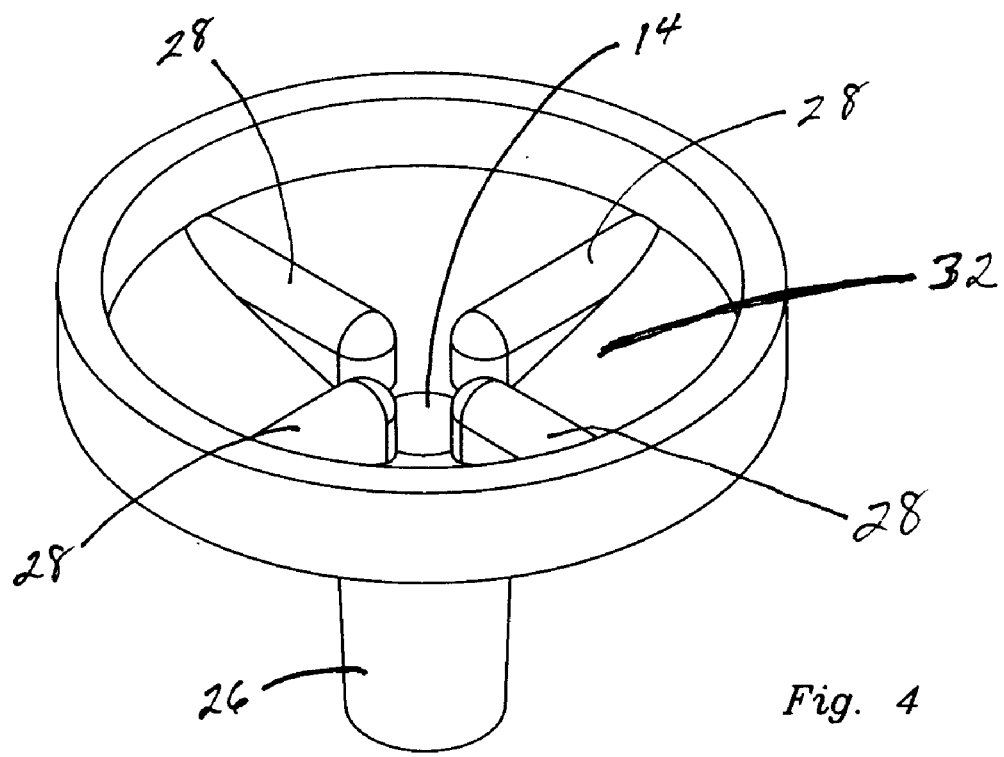
FIG. 4 is an illustration of a perspective view of the detail of FIG. 2.

FIG. 4 depicts a perspective detailed view of the portion of the housing of this embodiment adjacent to the sample exit 14. It may be seen more clearly here that a channel 32 is formed between spaced projections 28 of the invention. In a preferred embodiment shown, a series of four channels 32 located at about 90° angles to each other are disposed at the bottom of the housing and have a minimum width of about 0.062 inches. These channels 32 follow the downward slope of the housing, or inward turning 30, and end at the sample exit 14. This arrangement has been found to result in more uniform flow through a sorbent material being used in the housing.

Figure 5:
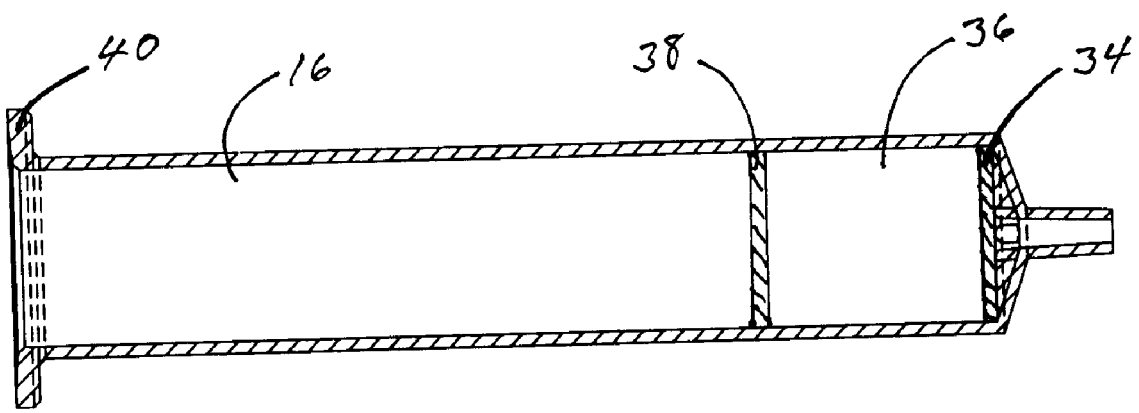
FIG. 5 is an illustration of a sectional side view of the embodiment of FIG. 1, illustrated with a sorbent and a sorbent retaining member within the housing.

FIG. 5 depicts a sectional view of the same embodiment of FIG. 1, but with a sorbent retaining member 34 and a sorbent 36 in place for use within the passageway 16. An optional porous capping member 38 is also shown disposed above the sorbent 36. The sorbent 36 is preferably a particulate sorbent, such as a silica or modified silica as known in the art of sample preparation. The porous capping member 38 can be made of a porous material that is impervious to a fluid used as a solvent, and that has pores for fluid passage that are sufficiently small to retain the sorbent. Especially preferred for the material of the porous capping member 38 is polyethylene of from about 125 to about 205 micron porosity.

The sorbent retaining member 34 may made of polyethylene, stainless steel, PTFE or other material known in the art that is capable of retaining sorbent material while minimizing contamination of a sample or a fluid used with the article. The member should be sufficiently porous to allow a fluid to pass through the member, but having a pore size selected to allow retention of a sorbent material that a user desires to use in the inventive cartridge. The sorbent retaining member 34 and the porous capping member 38 may be made of the same material, or of different materials.

It is especially preferred that the sorbent retaining member 34 comprise two materials, in the form of layers. Especially preferred is a lower layer of porous polyethylene, having an upper layer of glass microfiber laid upon the lower layer.

It a preferred embodiment, the sorbent is particulate, with a particle size of about 125 to about 210 microns.

In FIG. 5 may also be seen an optional flange 40 that extends radially from the sample entrance 12. This flange 40 may be used for gripping the housing 10, or for mounting it in a holding device while being used.

The present invention is not to be limited in scope by the embodiments disclosed herein, which are intended as single illustrations of one aspect of the invention, and any which are functionally equivalent are within the scope of the invention. Indeed, various modifications of the invention, in addition to those shown and described herein, will become apparent to those skilled in the art from the foregoing description. Such modifications are intended to fall within the scope of the appended claims.

We claim:

1. A housing of unitary construction for containing a sorbent used in chemical analysis, comprising:

a hollow tubular body member, said hollow tubular body member having a top end and a bottom end, and an interior wall and an exterior wall, said top end being open for receiving a sorbent and samples for chemical analysis, said bottom end having a convex end cap thereon, said convex end cap having an interior surface and an exterior surface, and an aperture therethrough, said convex end cap forming a sloping profile from said interior wall to said aperture, said interior surface of said convex end cap having a plurality of raised projections thereon, said raised projections being spaced apart to provide a plurality of channels therebetween for communication of a fluid to said aperture.

2. The housing according to claim 1, further comprising a porous sorbent retaining member, the porous sorbent retaining member being disposed on and supported by the plurality of raised projections.

3. The housing according to claim 2, further comprising a sorbent, disposed above the sorbent retaining member, the sorbent being particulate.

4. The housing according to claim 3, further comprising a porous capping member, disposed above the sorbent.

5. The housing according to claim 4, wherein the sorbent retaining member comprises: a first layer and a second layer disposed above the first layer, the first layer being a porous polyethylene disk, and the second layer being fibrous glass.

6. The housing according to claim 5, wherein the porous capping member is a polyethylene disk.

7. The housing according to claim 3, wherein said sorbent is selected from the group consisting of silica and modified silica.

8. The housing according to claim 1, wherein said hollow body member is cylindrical.

9. The housing according to claim 1, wherein said aperture comprises a Luer™ fitting located on said exterior surface of said convex end cap.

10. The housing according to claim 9, wherein said Luer™ fitting is a male fitting.

11. The housing according to claim 1, further comprising a flange, said flange being located at said top end of said body member and extending from said exterior wall.

12. A housing for containing a sorbent used in chemical analysis, comprising:

a hollow tubular body member of unitary construction, said hollow tubular body member having a top end and a bottom end, and an interior wall and an exterior wall, said top end being open for receiving a sorbent and samples for chemical analysis, said bottom end having a convex end cap thereon, said convex end cap having an interior surface and an exterior surface, and an aperture therethrough, said aperture comprising a male Luer™ fitting located on said exterior surface of said convex end cap, said convex end cap forming a sloping profile from said interior wall to said aperture, said interior surface of said convex end cap having a plurality of raised projections thereon, said plurality of raised projections extending radially from said aperture and forming a supporting profile that is substantially planar, said raised projections being spaced apart to provide a plurality of channels therebetween for communication of a fluid to said aperture, a porous sorbent retaining member, said porous sorbent retaining member being disposed on and supported by said plurality of raised projections, a sorbent disposed above said sorbent retaining member, and a porous sorbent capping member, said porous sorbent capping member being disposed above said sorbent and being parallel to said sorbent retaining member.

13. The housing according to claim 12, wherein said sorbent is selected from the group consisting of silica and modified silica.

14. The housing according to claim 12, wherein said porous sorbent retaining member comprises a first layer and a second layer, said first layer comprising a porous polyethylene disk, said second layer comprising fibrous glass.

15. The housing according to claim 12, wherein said porous sorbent capping member comprises a polyethylene disk.

* * * * *